United States Patent [19]
deMey, II

[11] 4,233,657
[45] Nov. 11, 1980

[54] SOURCE LAMP POSITIONING APPARATUS

[75] Inventor: Charles F. deMey, II, West Redding, Conn.

[73] Assignee: The Perkin-Elmer Corporation, Norwalk, Conn.

[21] Appl. No.: 8,916

[22] Filed: Feb. 2, 1979

[51] Int. Cl.³ ............................................. F21V 23/04
[52] U.S. Cl. ................................. 362/396; 362/294; 362/398; 362/421; 362/428
[58] Field of Search ............... 362/396, 418, 421, 429, 362/428, 398, 294

[56] References Cited
U.S. PATENT DOCUMENTS

| | | | |
|---|---|---|---|
| 3,873,823 | 3/1975 | Northrup et al. | 362/396 X |
| 3,906,217 | 9/1975 | Lackore | 362/396 X |

Primary Examiner—Stephen J. Lechert, Jr.
Attorney, Agent, or Firm—S. A. Giarratana; F. L. Masselle; E. T. Grimes

[57] ABSTRACT

Apparatus for clampingly supporting a source lamp in an optical, analytical instrument. The apparatus includes a heat distributing, metal corset encircling the lamp and a clamp member. The clamp is adjustably mounted in the instrument by a mechanism which permits rotational adjustment of the clamp about an axis perpendicular to the optical axis of the instrument and translational adjustment of the clamp along the same axis. The lamp is supported in the clamp in a stable configuration regardless of irregularities in its glass envelope.

14 Claims, 10 Drawing Figures

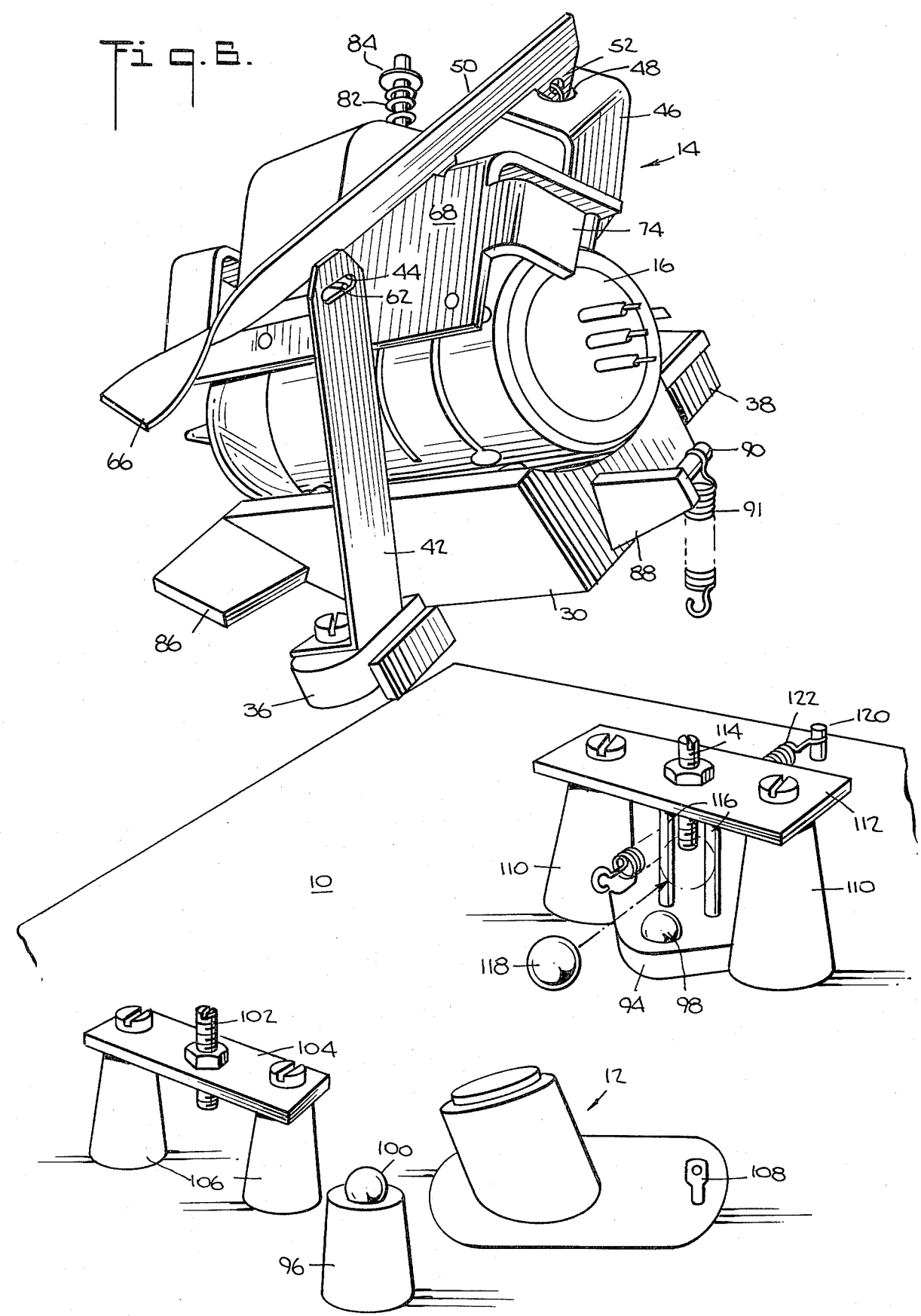

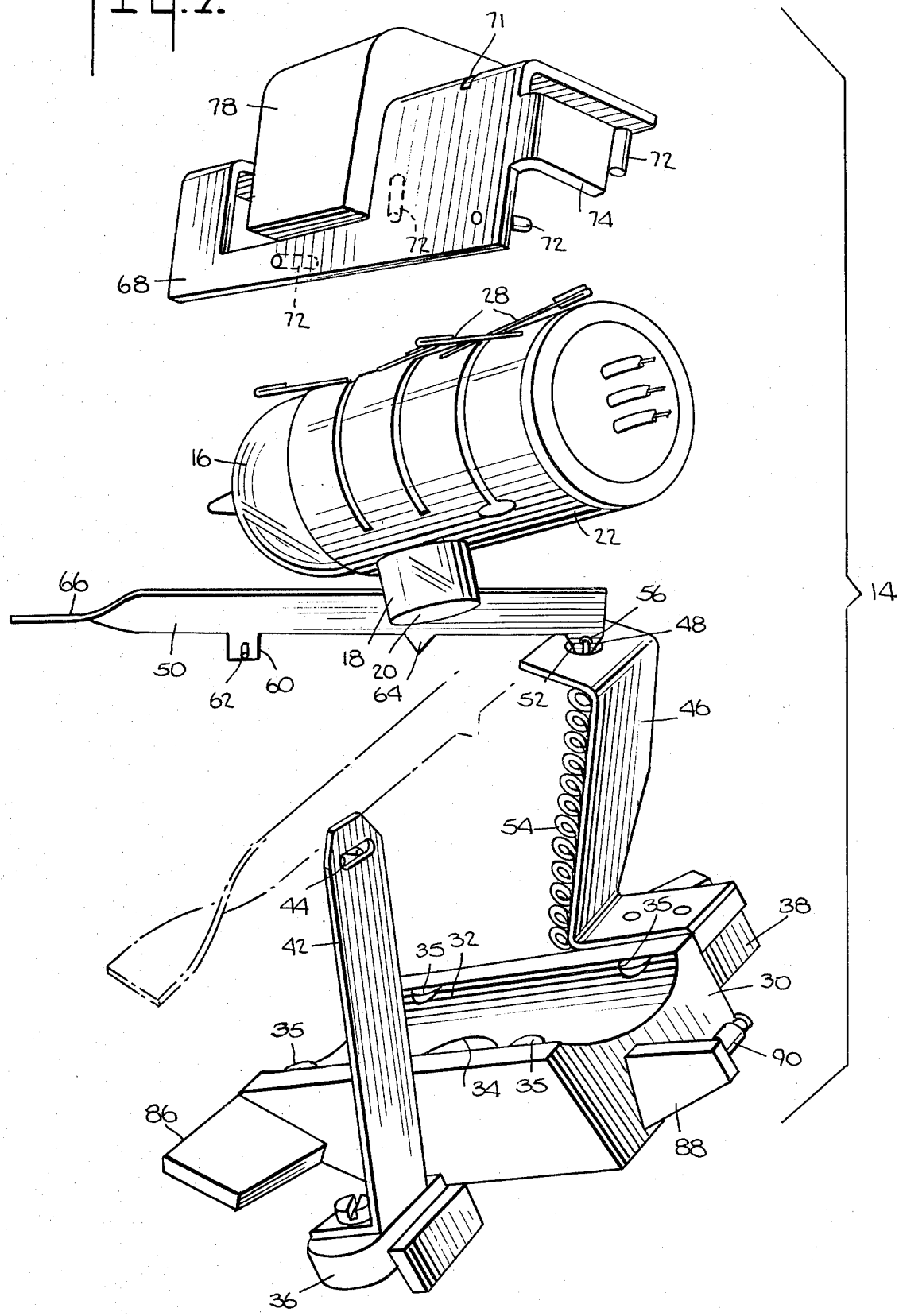

SOURCE LAMP POSITIONING APPARATUS

BACKGROUND OF THE INVENTION

Many optical instruments require the use of a source lamp for producing radiation in a selected wavelength range. An example of such an instrument is an absorption photometer. An exemplary source lamp would comprise a substantially cylindrical glass or quartz envelope with a cylindrical protrusion, or "snout" extending from the side and defining the exit window. The actual radiation source within the lamp is very small, approximately one millimeter in diameter. When the lamp is installed within the instrument, the source must be exactly aligned with the optical axis of the instrument to provide maximum energy transfer. This adjustment may be made, although not without difficulty, when the instrument is assembled by the manufacturer. However, it is often necessary to change source lamps in the field, either because of failure or deterioration of the original lamp, or to substitute a lamp having a different wavelength emission range. This is when problems often arise due to the fact that the glass or quartz envelopes vary from lamp to lamp, resulting in corresponding variations in mechanical positioning and in the optical characteristics acting upon the source. Source lamp holders, in accordance with the prior art, are adjustable to compensate for these variations, but the adjustments are quite tedious and time-consuming and require the making of a number of separate but interrelated adjustments.

Still another problem which arises with prior art lamp holders is that the lamps tend to heat non-uniformly, thereby creating undesirable optical variations, especially during extended operation.

Accordingly, it is a primary object of the present invention to provide an improved, adjustable lamp holder for use with optical analytical instruments. Other objects are to provide such a holder wherein the heat distribution characteristics of the lamp are improved, wherein lamps are quickly and easily interchanged, and wherein the lamp position may be easily and quickly adjusted so that its radiation source is precisely aligned with the optical axis of the instrument. The manner in which the foregoing objects are achieved will be apparent from the following description and appended claims.

SUMMARY OF THE INVENTION

An improvement in an optical apparatus which includes a base member, a radiation source lamp, and a holder for adjustably positioning the lamp to direct radiation along a preselected optical axis. The improvement comprises first and second pivot members intermediate the base member and holder on an axis of rotation which is substantially perpendicular to the optical axis. Means intermediate the base member and holder define a linear groove which is parallel to the axis of rotation and receives the first and second pivot members therein. Means are provided for resiliently urging the holder in a first direction of rotation about the axis of rotation. Other means are provided which adjustably restrain the holder from rotation in the first direction of rotation. Other means are provided for adjustably translating the holder along the axis of rotation by linear relative movement between the groove and the first and second pivot members.

BRIEF DESCRIPTION OF THE DRAWINGS

FIG. 3 is a cross-section taken substantially along the line 3—3 of FIG. 1;

FIG. 7 is an exploded perspective view of the lamp holder and lamp;

FIG. 8 is an exploded perspective view of a portion of the lamp holder and the magnet associated therewith;

DESCRIPTION OF THE PREFERRED EMBODIMENT

Figure 1:
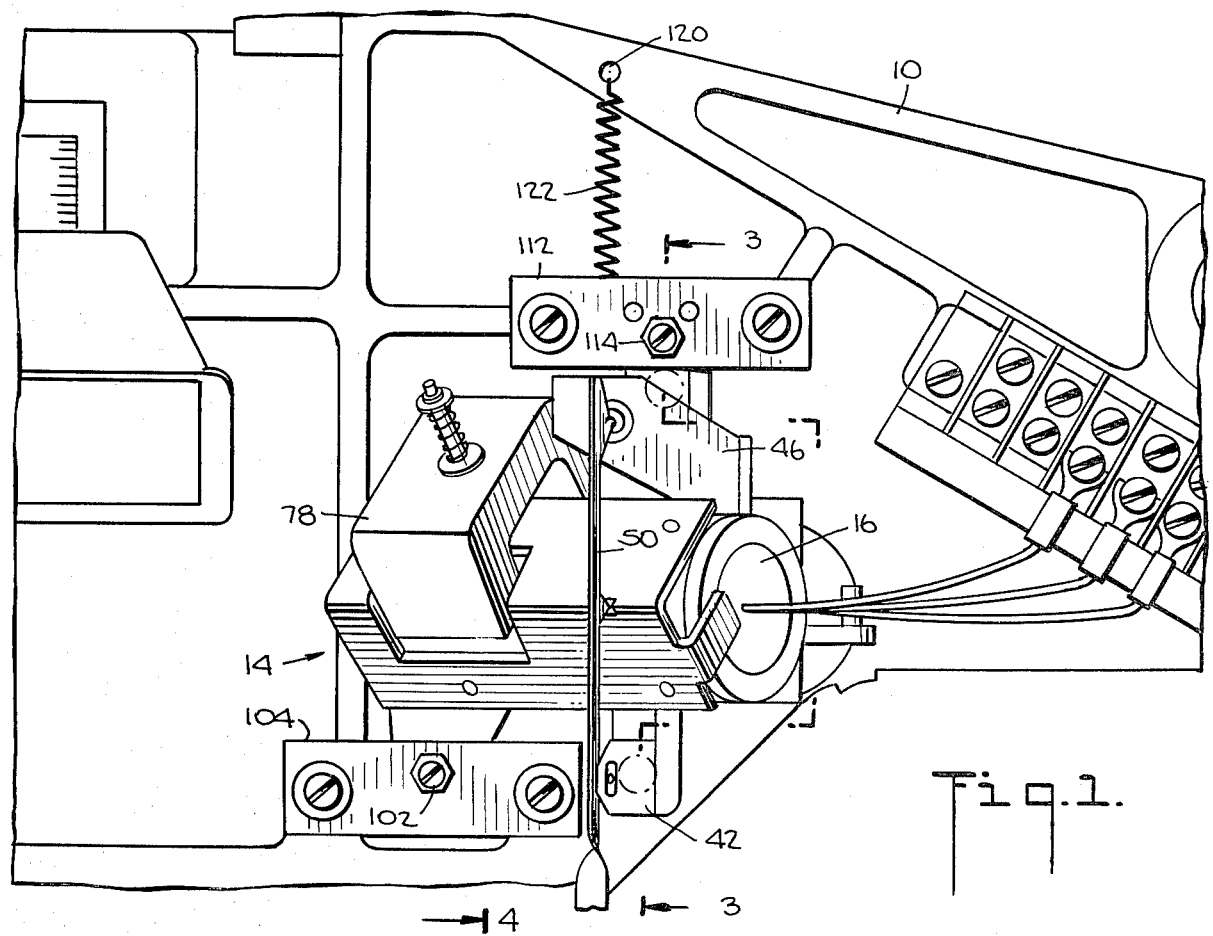
FIG. 1 is a plan view of a portion of the base of an analytical instrument with a lamp holder in accordance with the present invention mounted thereon.
Figure 9:
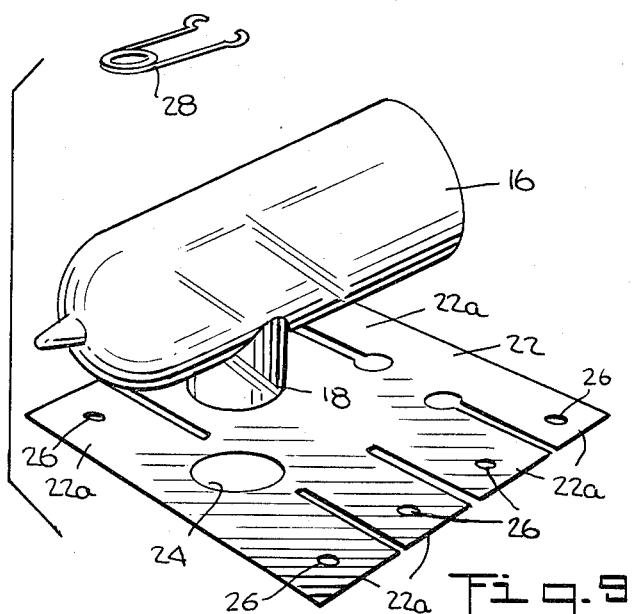
FIG. 9 is an exploded perspective view of a source lamp, its heat distributing corset, and one of the corset torsion clamping springs; and, FIG. 10 is a plan view of the lamp of FIG. 9 with its corset secured thereto.
Figure 10:
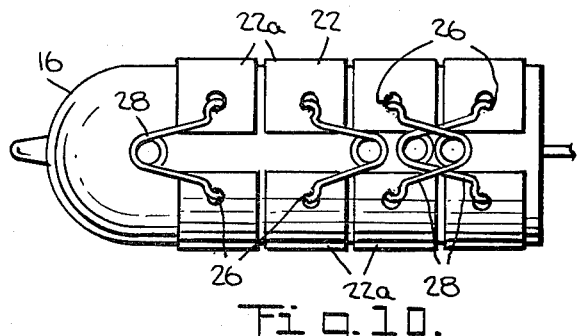

With particular reference to FIGS. 1 and 3, there is illustrated a base casting 10 of an optical instrument which carries a light tunnel assembly 12 (FIG. 4) which encloses a portion of the optical axis OA of the instrument. Mounted on the base casting 10, by means of an adjusting mechanism to be described, is a lamp holder assembly 14 securing a source lamp 16, such as a deuterium lamp. The source lamp 16 is of conventional configuration being in the form of a glass or quartz cylinder having a smaller diameter cylindrical snout 18, including a planar end window 20 for exiting radiation. The lamp may, if desired, be provided with an ozone absorbence controller of the type disclosed in U.S. Pat. No. 4,049,987. In order to improve the heat distribution characteristics of the glass envelope of source lamp 16, there is provided a heat conductive corset 22 as shown in FIG. 9 made of a material such as aluminum. The corset 22 is in the form of a thin plate and defines an opening 24 for the lamp snout 18. The edges of the corset 22 are pierced to form a plurality of tabs 22a, each of which is pierced by a hole 26. The snout 18 is passed through the opening 24 and the tabs 22a wrapped tightly around the lamp 16. The corset is secured in place by means of a plurality of torsion springs 28 which engage holes 26 as shown in FIG. 10.

LAMP HOLDER ASSEMBLY

Figure 6:
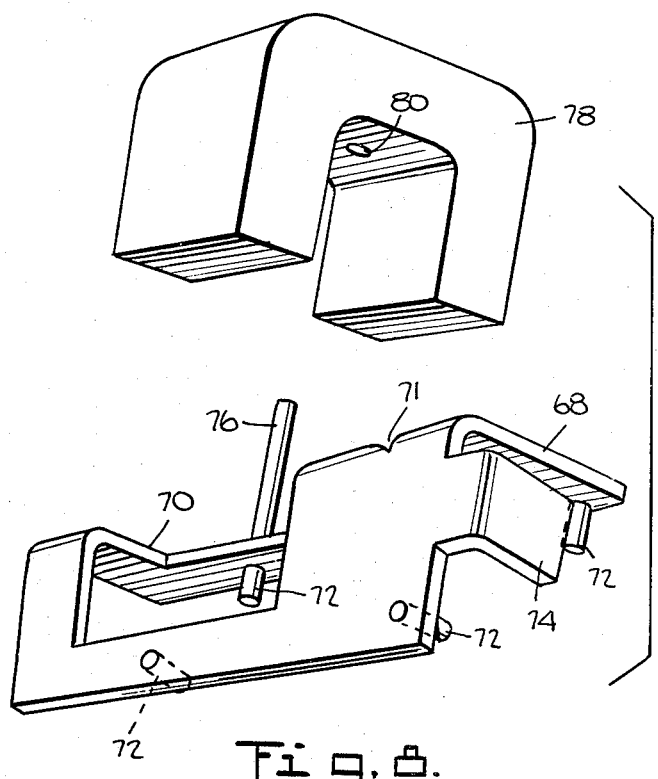
FIG. 6 is an exploded perspective view showing the lamp holder and lamp separated from the adjustable mounting.

The lamp holder assembly per se is shown most clearly in FIGS. 6 and 7. It comprises a cradle block 30 having a cylindrical lamp engaging recess 32 on one surface and a transverse opening 34 for the snout 18 of lamp 16. A pair of spaced lugs 35 (FIG. 7) extend into each side of recess 32 from the upper surface of cradle block 30. The opening 34 is semicircular in part but, as shown in FIG. 3, has V-shaped side walls 34a toward the lower end. A pair of arms 36, 38 extend outwardly from either side of the cradle block 30 and the bottom surfaces of these arms include co-linear V-grooves 40 (FIG. 3).

An elongated clip member 42 is mounted on arm 36 and extends upwardly therefrom and defines a latch opening 44 at its upper end. Mounted upon the arm 38 is a generally Z-shaped bracket 46 which is generally parallel to the clip member 42. The upper end of the bracket 46 includes a circular opening 48. Extendable between the bracket 46 and clip member 42 is a locking lever 50. At one end, lever 50 carries a triangular projection 52 which is pivotally mounted in the opening 48 where it is retained by means of a spring 54 which extends between a hole 56 in projection 52 and a spade bolt 58 on arm 38 (FIG. 3). Spaced from the projection 52 by a distance approximating that between the bracket 46 and the clip member 42 is a downwardly extending tab 60 from which extends a locking pin 62 engageable in the latch opening 44. Intermediate the projection 52 and tab 60 is a triangular clamping projection 64, the function of which will be described below. The end of the lever 50 is twisted to form a finger grip 66.

Figure 5:
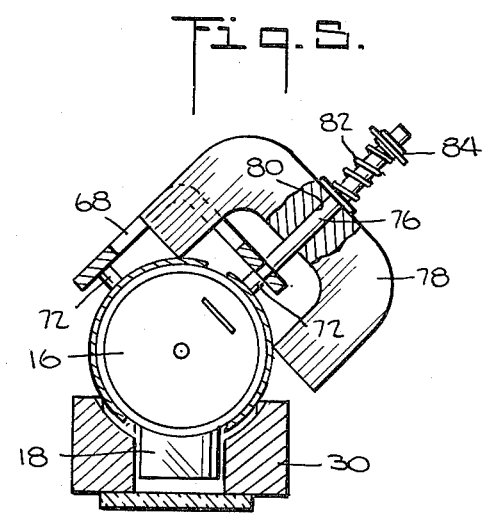
FIG. 5 is a cross-section taken substantially along the line 5—5 of FIG. 4.

Completing the lamp holder assembly 14 is an upper clamp member 68 which is most clearly illustrated in FIG. 8. Clamp member 68 is L-shaped in cross-section and includes a central aperture 70. The angle of the L includes a notch 71. Four pins 72 extend inwardly from the two arms of the L-shaped clamp member so as to engage the lamp 16, as illustrated in FIG. 5. In addition, the clamp member 68 includes an end tab 74 positioned to engage the end of the lamp 16 as shown in FIG. 6.

One of the pins 72 includes an elongated, upwardly extending projection forming a post 76. A permanent horseshoe magnet 78 has a central passage 80 which receives the post 76 so that the magnet is positionable in close proximity to the lamp 16, as shown in FIG. 5. The magnet is retained in this position by means of a compression spring 82 and clip 84 assembly.

Figure 4:
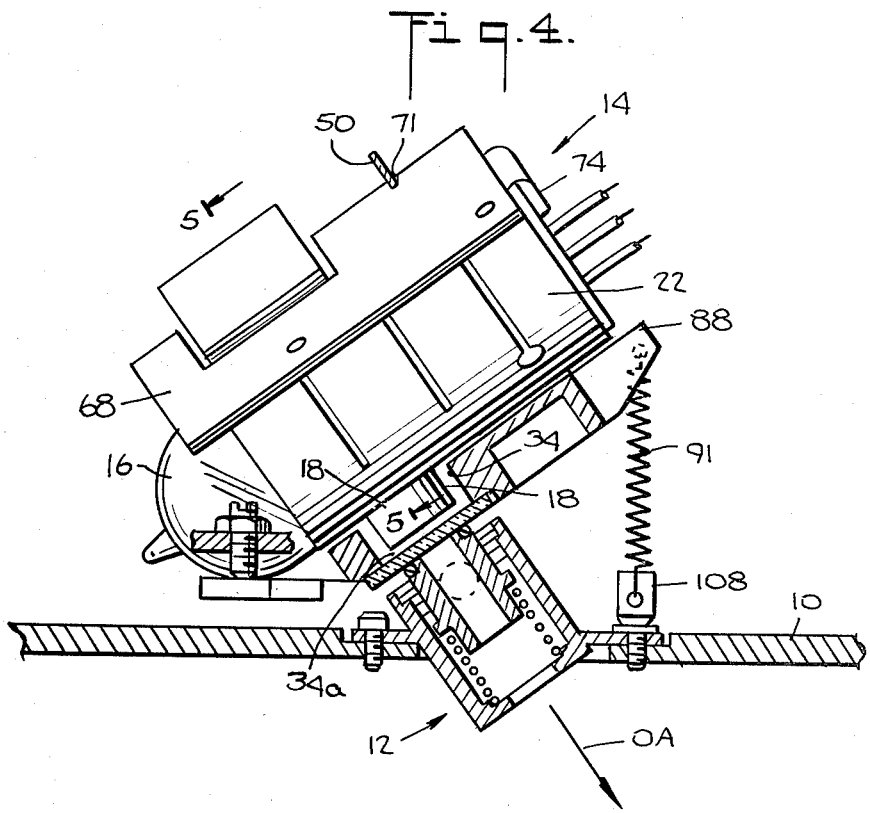
FIG. 4 is a cross-section taken substantially along the line 4—4 of FIG. 3.

It is believed that the assembly of the lamp holder will be apparent from FIGS. 6 and 7. The lamp 16 is positioned on the lugs 35 in the recess 32 of cradle block 30 with its snout 18 extending into the opening 34. Since the glass envelope only makes point contact with the lugs 35 rather than with the surface of recess 32, positional instability resulting from bulges, bumps, etc., of the envelope is substantially eliminated. Upper clamp member 68, with its attached magnet 78, is mounted on top of lamp 16 with the end of the lamp being engaged by the end tab 74. The lever 50 is then pivoted over the top of the clamp member 68 and pressed downwardly to engage the locking pin 62 in the latch opening 44. The clamping projection 64 engages the recess 71 which acts as a fulcrum, slightly stretching the spring 54 to securely retain the lamp within the assembly. Referring to FIG. 4, it will be noted that spring loaded lever 50 exerts force downward and to the left. The end tab 74 forces the snout 18 of the lamp to seat against the V-shaped walls 34a where it is accurately retained along two contact lines.

The entire lamp holder assembly is designed to be adjustable as a unit. To this end, there are provided certain elements which are not necessary to the function of clamping the lamp. These include, for example, a tilt plate 86 which extends outwardly from one end of the cradle block 30, and a support arm 88 at its other end carrying a spring post 90. One end of a tension spring 91 is connected to post 90. In addition, the arm 38 includes an angled camming surface 92, as shown in FIG. 3.

ADJUSTABLE MOUNTING

The lamp holder and lamp assembly 14 is retained within the instrument by means of an adjustable mounting. This mounting is extremely stable by virtue of its three point support. However, the assembly is adjustable rotatably about a line passing through two of the support points and is linearly adjustable along such line. In order to provide for the requisite three point support, the base casting 10 includes a pair of ball bearing support projections 94, 96 which can be seen most clearly in the exploded view of FIG. 6. The upper surface of each projection defines a depression within which is seated a respective bearing ball 98, 100. A line passing through the bearing balls 98, 100 is perpendicular to the optical axis OA passing through light tunnel assembly 12. A third support point is provided by the lower end of an adjusting screw 102 mounted in a horizontal support plate 104 which is elevated above the base casting 10 by a pair of spaced pillars 106. On the opposite side of the line joining bearing balls 98, 100 from the adjustment screw 102 is a spring attachment in the form of a spade bolt 108.

Positioned above the bearing ball 98, by means of a pair of spaced pillars 110, is a horizontal support plate 112 through which extends a vertical adjusting screw 114 with its lower end spaced above the support projection 94. Immediately behind the adjusting screw 114 are a pair of spaced vertical guide bars 116. A linear adjustment ball 118 is normally mounted to ride vertically against the guide bars 116 under the influence of adjusting screw 114 as will be explained below. Mounted in the base casting 10 and behind the guide bars 116 is a vertical pin 120 to which is secured one end of a coil spring 122.

ASSEMBLY AND ADJUSTMENT

In assembling the lamp holder, the magnet 78 is mounted on the upper clamp member 68 with its central passage 80 receiving the post 76. The spring 82 is positioned over the post and its upper end compressed downwardly and secured by means of clip 84. The source lamp, with its corset secured, is positioned on the lugs 35 in cradle block 30. The upper clamp member 68 is positioned on top of the source lamp and the lever 50 is pivoted into position and latched, as previously explained, to the clip member 42. In this manner, the source lamp is rigidly secured within the assembly. The function of the magnet 78 is known in the prior art. It is to attract and thereby stabilize the internal magnetic elements of the source lamp so as to prevent their displacement by vibration or otherwise. It also serves to stabilize the arc.

Figure 2:
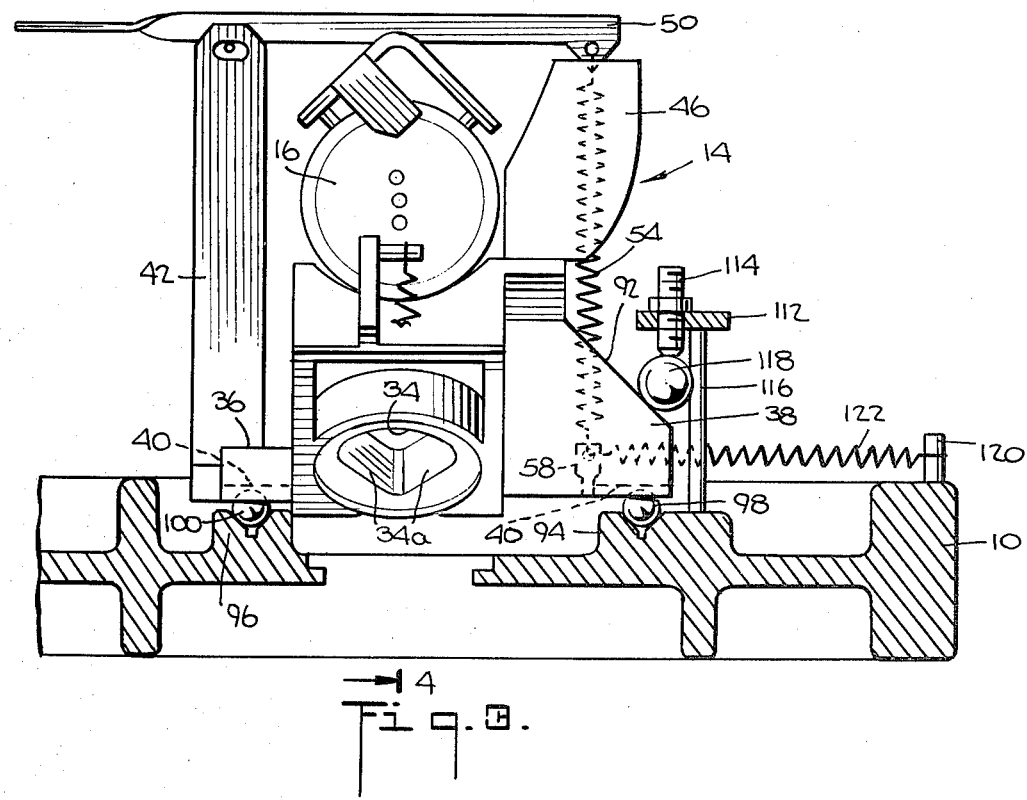
FIG. 2 is an enlarged perspective view of the lamp holder of FIG. 1.
Figure 2:
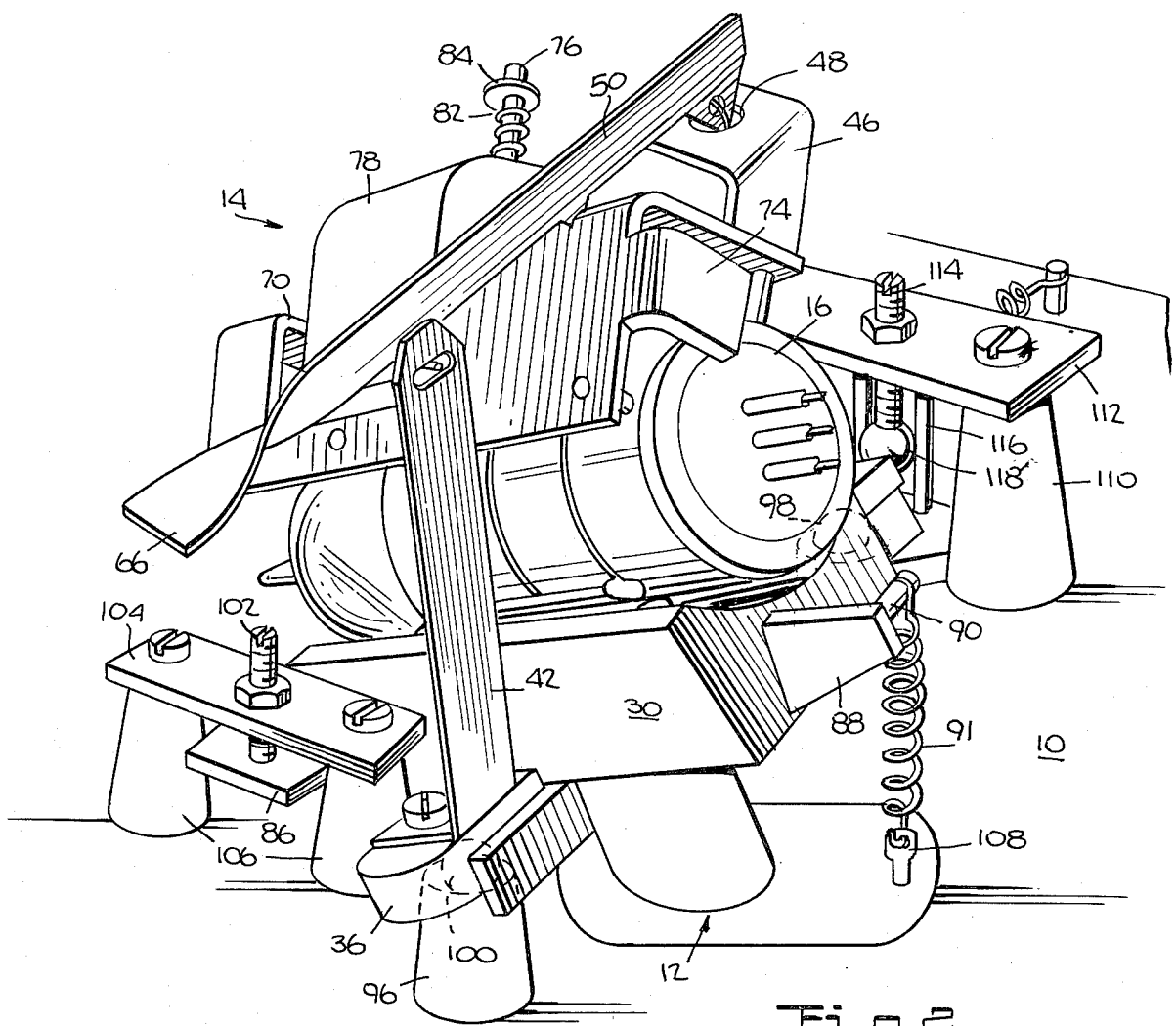

The lamp holder assembly 14 is next positioned on the adjusting mechanism. Referring to FIGS. 2 and 6, this is accomplished by positioning the V-shaped grooves in the bottoms of arms 36 and 38 on the bearing balls 100, 98. At the same time, the tilt plate 86 is positioned beneath the adjusting screw 102. The spring 91 is stretched and hooked between the spring post 90 on the lamp holder assembly and the spade bolt 108 in the base casting.

As the lamp holder assembly 14 is being positioned on the three point support formed by balls 98 and 100 and adjusting screw 102, the linear adjustment ball 118 is also placed in position beneath the adjusting screw 114 and against the guide bars 116 while simultaneously bearing against the camming surface 92 (FIG. 3). Thereafter, the spring 122 is stretched and secured between the spade bolt 58 and the pin 120.

By means of the disclosed construction, the lamp holder assembly 14 is adjustable as to tilt by a simple adjustment of screw 102. This screw bears downwardly against the tilt plate 86 and against the tension of spring 91, which tends to rotate the assembly in a clockwise direction as viewed in FIG. 2. The spring thereby serves both to rotate the lamp holder assembly and to take up any slack or play in the adjusting screw threads.

Linear transverse adjustment is provided by the linear adjustment ball 118, as seen in FIG. 3. This ball rides within the "track" formed by guide bars 116 and against the camming surface 92. Spring 122 tends to cause the lamp assembly to move to the right, as viewed in FIG. 3. However, adjustment of screw 114 will cause the ball 118 to be lowered or raised to thereby actuate the camming surface 92 to the left or right. This, in turn, will cause the lamp holder assembly 14, by its V-grooves 40, to be shifted upon the bearing balls 98, 100. It will be noted that, by means of this construction, both adjusting screws 102 and 114 are accessible from the same side of the instrument, even though they control adjustment in two different degrees of freedom.

It is believed that the many advantages of this invention will now be apparent to those skilled in the art. By means of this invention, there is provided a very stable three point support for a lamp holder assembly and, at the same time, a simple two screw adjustment for positioning a source lamp for maximum energy transfer. Under field conditions, it is a simple matter for a user to make these adjustments. If the instrument electronics are energized, maximum energy transfer may be achieved by observing the output meter level.

It will also be apparent to those skilled in the art that a number of variations and modifications may be made in this invention without departing from its spirit and scope. Accordingly, the foregoing description is to be construed as illustrative only, rather than limiting. This invention is limited only by the scope of the following claims.

We claim:

1. In an optical apparatus including a base member, a substantially cylindrical radiation source lamp having a sidewardly projecting cylindrical protrusion, and a holder for adjustably positioning said lamp to direct radiation along a preselected optical axis, the improvement which comprises: first and second pivot members intermediate said base member and holder on an axis of rotation substantially perpendicular to said optical axis; means intermediate said base member and holder defining a linear groove parallel to said axis of rotation and receiving said first and second pivot members therein; means for resiliently urging said holder in a first direction of rotation about said axis of rotation; means for adjustably restraining said holder from rotation in said first direction of rotation; and means for adjustably translating said holder along said axis of rotation by linear relative movement between said groove and said first and second pivot members.

2. The improvement of claim 1 wherein said resilient urging means comprises a spring and said adjustable restraining means comprises a screw.

3. The improvement of claim 1 wherein said base member defines a pair of depressions, said first and second pivot members comprise ball members positioned therein, and said holder defines said linear groove.

4. The improvement of claim 1 wherein said holder comprises: a cradle block for supporting one side of said source lamp therein; a clamp member spaced from said cradle block and positionable on the opposite side of said source lamp; and means for resiliently engaging said clamp member and said cradle block to secure said source lamp therebetween.

5. The improvement of claim 4 wherein said engaging means comprises: a lever having a central fulcrum point for engaging said clamp member; means for detachably engaging a first end of said lever with said cradle block; and spring means intermediate a second end of said lever and said cradle block.

6. The improvement of claim 4 wherein said clamp member includes a magnet positioned in close proximity to said source lamp.

7. The improvement of claim 4 wherein said cradle block defines a lamp-receiving recess therein including a plurality of lamp supporting projecting lugs and further defines a transverse protrusion receiving opening therethrough.

8. The improvement of claim 7 wherein said engaging means comprises: a lever having a central fulcrum point for engaging said clamp member; means for detachably engaging a first end of said lever with said cradle block; and spring means intermediate a second end of said lever and said cradle block.

9. The improvement of claim 8 wherein said protrusion receiving opening is formed to engage said protrusion along two substantially parallel contact lines on the cylindrical surface of said protrusion.

10. The improvement of claim 9 wherein said spring means urges said protrusion into engagement with said protrusion receiving opening along said contact lines.

11. The improvement of claim 1 wherein said translating means comprises: first linear track means supported by said holder; second linear track means supported by said base member and angled relative to said first track means; a ball member intermediate, and in contact with, both of said first and second track means; resilient means for urging said holder in a first direction along said axis of rotation relative to said base member; and means for advancing said ball member intermediate said first and second track means to urge said holder in a second direction along said axis of rotation.

12. The improvement of claim 11 wherein said advancing means comprises a screw.

13. The improvement of claim 11 wherein said first track member comprises a camming surface on said holder and said second track member is substantially perpendicular to the direction of translation along said axis of rotation.

14. The improvement of claim 13 wherein said second track member comprises: a pair of spaced, parallel guide bars supporting said ball member therebetween.

* * * * *